United States Patent
Schelges et al.

(10) Patent No.: US 10,357,442 B2
(45) Date of Patent: Jul. 23, 2019

(54) SURFACTANT-CONTAINING CLEANSING AGENTS WITH AT LEAST FOUR DIFFERENT PRESERVATIVES

(71) Applicant: Henkel AG & Co. KGaA, Duesseldorf (DE)

(72) Inventors: Heike Schelges, Willich (DE); Rainer Simmering, Grevenbroich (DE); Barbara Heide, Krefeld (DE); Melanie Rauschenberg, Kamen (DE)

(73) Assignee: Henkel AG & Co. KGaA (DE)

(*) Notice: Subject to any disclaimer, the term of this patent is extended or adjusted under 35 U.S.C. 154(b) by 0 days.

(21) Appl. No.: 15/372,504

(22) Filed: Dec. 8, 2016

(65) Prior Publication Data

US 2017/0165169 A1 Jun. 15, 2017

(30) Foreign Application Priority Data

Dec. 11, 2015 (DE) .................. 10 2015 225 004

(51) Int. Cl.

| | |
|---|---|
| *C11D 3/48* | (2006.01) |
| *A61K 8/49* | (2006.01) |
| *A61K 8/23* | (2006.01) |
| *A61K 8/33* | (2006.01) |
| *A61K 8/34* | (2006.01) |
| *A61K 8/36* | (2006.01) |
| *A61K 8/368* | (2006.01) |
| *A61K 8/42* | (2006.01) |
| *A61K 8/43* | (2006.01) |
| *A61K 8/44* | (2006.01) |
| *A61K 8/46* | (2006.01) |
| *A61K 8/60* | (2006.01) |
| *A61Q 19/10* | (2006.01) |
| *A61K 8/31* | (2006.01) |
| *A61K 8/365* | (2006.01) |
| *A61K 8/37* | (2006.01) |
| *A61Q 5/02* | (2006.01) |
| *A61Q 17/00* | (2006.01) |
| *A61K 8/86* | (2006.01) |
| *A61K 8/06* | (2006.01) |

(52) U.S. Cl.
CPC .............. *A61K 8/4953* (2013.01); *A61K 8/06* (2013.01); *A61K 8/23* (2013.01); *A61K 8/31* (2013.01); *A61K 8/33* (2013.01); *A61K 8/34* (2013.01); *A61K 8/347* (2013.01); *A61K 8/36* (2013.01); *A61K 8/361* (2013.01); *A61K 8/365* (2013.01); *A61K 8/368* (2013.01); *A61K 8/37* (2013.01); *A61K 8/375* (2013.01); *A61K 8/42* (2013.01); *A61K 8/43* (2013.01); *A61K 8/44* (2013.01); *A61K 8/442* (2013.01); *A61K 8/46* (2013.01); *A61K 8/463* (2013.01); *A61K 8/494* (2013.01); *A61K 8/4926* (2013.01); *A61K 8/4946* (2013.01); *A61K 8/602* (2013.01); *A61K 8/86* (2013.01); *A61Q 5/02* (2013.01); *A61Q 17/005* (2013.01); *A61Q 19/10* (2013.01); *A61K 2800/524* (2013.01); *A61K 2800/592* (2013.01); *A61K 2800/5922* (2013.01)

(58) Field of Classification Search
CPC ........... C11D 1/62; C11D 3/0084; C11D 3/48; C11D 3/2034
See application file for complete search history.

(56) References Cited

U.S. PATENT DOCUMENTS

| | | | | |
|---|---|---|---|---|
| 2006/0115440 A1* | 6/2006 | Arata et al. | ............ | A61K 8/365 424/65 |
| 2007/0248561 A1* | 10/2007 | Milbradt | ................ | A61K 8/042 424/70.16 |
| 2009/0123577 A1* | 5/2009 | Beilfuss et al. | ......... | A61K 8/30 424/729 |

FOREIGN PATENT DOCUMENTS

| | | |
|---|---|---|
| EP | 1414394 B1 | 6/2009 |
| WO | 03/043593 A1 | 5/2003 |
| WO | 2007/014580 A1 | 2/2007 |

\* cited by examiner

*Primary Examiner* — Charles I Boyer
(74) *Attorney, Agent, or Firm* — James J. Cummings

(57) ABSTRACT

Cleansing compositions include at least one special preservative combination. The cleansing compositions are used for the cleaning and/or care of skin and/or hair, and specific preservative combination is used for preserving such surfactant-containing cleansing compositions.

13 Claims, No Drawings

SURFACTANT-CONTAINING CLEANSING AGENTS WITH AT LEAST FOUR DIFFERENT PRESERVATIVES

FIELD OF THE INVENTION

The present invention generally relates to cleansing agent compositions, which include, apart from at least one surfactant, at least one special preservative combination and in addition at least one other preservative. Furthermore, the present invention relates to the use of such cleansing compositions for the cleansing and care of skin and/or hair.

BACKGROUND OF THE INVENTION

Because of their composition, cosmetic agents can be a nutrient medium for bacteria and microorganisms. These bacteria, on the one hand, can cause the microbial contamination of the user, and, on the other, they can change the ingredients of the cosmetics and thereby form substances with undesirable effects such as sensitization or skin irritation. In order to prevent these undesirable consequences and to assure a specific minimum durability of the cosmetics, they must be preserved. Because preservative for their part have an irritation potential, their use in cosmetics is strictly regulated.

Skin microflora has a decisive effect on various cosmetic parameters. Thus, pathogenic bacteria such as *Staphylococcus aureus* play a decisive role in the formation of skin impurities. Most recent studies also point out that an unbalanced skin microflora can exert an effect on skin aging, because undesirable bacteria can lead to an increased immune defense of the skin, which in turn leads to increased inflammatory reactions during which skin aging markers are stimulated.

There continues to be a need for preservative compositions, therefore, that, on the one hand, prevent the colonizing of the product or skin with undesirable bacteria and, on the other, do not or do not substantially affect the natural skin flora.

The mixing of different antimicrobial substances to increase the antimicrobial activity is generally known. Thus, WO 03/043593 A1 proposes combining conventional antibacterial substances such as triclosan, phenoxyethanol, or hexetidine with ethyl lauroyl arginate to enhance the antibacterial action. In WO 2007/014580 A1, preservative mixtures are proposed, which, include, apart from ethyl lauroyl arginate salts of organic or inorganic acids, in particular sodium citrate, sodium acetate, sodium glutamate, sodium fumarate, sodium malate, sodium gluconate, sodium laurate, sodium lactate, sodium hexametaphosphate, sodium tert-butylhydroquinonate, sodium propylparabenate, or the hydrochlorides of glucosamine or ethanolamine. Cosmetic compositions, which include a preservative mixture of ethyl lauroyl arginate and parabens, imidazolyl urea, phenoxyethanol, DMDM hydantoin, 2-methyl-5-chloro-3,4-isothiazolinone/2-methyl-3,4-isothiazolinone, and quaternium-15, are disclosed in EP 1414394 B1.

Therefore, there continues to be the need for providing antimicrobial compositions that are highly effective when used in a low amount.

To summarize, it is desirable to provide cleansing compositions that have an excellent cleansing and care effect with simultaneously good preservation. In particular, it is desirable to provide synergistic preservative mixtures that are highly effective in low concentrations, and because of their overall reduced quantities enable the production of low-irritant and low-sensitizing cleansing compositions. Furthermore, no preservatives critically perceived by the consumer should be used. Moreover, the foam quality, foam quantity, and lather amount should not be negatively influenced by the addition of the preservative mixture to a cleansing composition.

Furthermore, other desirable features and characteristics of the present invention will become apparent from the subsequent detailed description of the invention and the appended claims, taken in conjunction with this background of the invention.

BRIEF SUMMARY OF THE INVENTION

A cleansing composition in a cosmetically acceptable carrier includes at least one surfactant, selected from the group of anionic surfactants, cationic surfactants, amphoteric surfactants, nonionic surfactants, and mixtures thereof; at least one preservative mixture, selected from the group of chloroxylenol and phenoxyisopropanol, undecylenic acid and formic acid, phenoxyisopropanol and piroctone olamine, phenoxyisopropanol and formic acid, sulfite(s) and hexetidine, ethyl lauroyl arginate and formic acid, ethyl lauroyl arginate and chloroxylenol, hexetidine and benzyl alcohol, hexetidine and chloroxylenol, hexetidine and piroctone olamine, hexetidine and chlorophenesin, hexetidine and formic acid, and mixtures thereof; and at least one other preservative, selected from the group of benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof, and mixtures of these preservatives.

At least one preservative mixture(s), selected from the group comprising chloroxylenol and phenoxyisopropanol, undecylenic acid and formic acid, phenoxyisopropanol and piroctone olamine, phenoxyisopropanol and formic acid, sulfite(s) and hexetidine, ethyl lauroyl arginate and formic acid, ethyl lauroyl arginate and chloroxylenol, hexetidine and benzyl alcohol, hexetidine and chloroxylenol, hexetidine and piroctone olamine, hexetidine and chlorphenesin, hexetidine and formic acid, and mixtures thereof is used in a method for preserving surfactant-containing cleansing compositions.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It was now found surprisingly that the use of certain mixtures of preservatives in surfactant-containing cleansing compositions leads to a synergistic effect in regard to the preservative action. For this reason, the amount of preservatives employed can be reduced without negatively influencing the preservative action. Because of the reduced amount of preservatives, the cleansing compositions of the invention are low in irritation and sensitization. Moreover, the addition of the preservative mixtures leads to an improved foam quality, foam quantity, and lather amount.

The subject of the present invention is a cleansing composition in a cosmetically acceptable carrier and that includes:
a) at least one surfactant, selected from the group that includes anionic surfactants, cationic surfactants, amphoteric surfactants, nonionic surfactants, and mixtures thereof and
b) at least one preservative mixture, selected from the group that includes
chloroxylenol and phenoxyisopropanol
undecylenic acid and formic acid
phenoxyisopropanol and piroctone olamine
phenoxyisopropanol and formic acid
sulfite(s) and hexetidine
ethyl lauroyl arginate and formic acid
ethyl lauroyl arginate and chloroxylenol
hexetidine and benzyl alcohol
hexetidine and chloroxylenol
hexetidine and piroctone olamine
hexetidine and chlorophenesin
hexetidine and formic acid,
and mixtures thereof and
c) at least one other preservative, selected from the group that includes benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof, and mixtures of these preservatives.

The term "preservative mixture" according to the invention is understood to mean a mixture of two of the preservatives previously listed under feature b).

The quantity given in % by weight in the present case, unless otherwise specified, refers to the total weight of the cleansing composition of the invention, the sum of all ingredients of the agents of the invention resulting in 100% by weight.

The cleansing composition of the invention includes as the first essential ingredient a) at least one surfactant, selected from the group comprising anionic surfactants, cationic surfactants, amphoteric surfactants, nonionic surfactants, and mixtures thereof.

The term "surfactant" according to the invention is understood to mean amphiphilic (bifunctional) compounds, which consist of at least one hydrophobic and at least one hydrophilic moiety. The hydrophobic group is preferably a hydrocarbon group having 8 to 28 carbon atoms, which may be saturated or unsaturated, linear or branched. Particularly preferably, this $C_8$-$C_{28}$ alkyl chain is linear.

Anionic surfactants are understood to be surfactants that include exclusively anionic charges. Surfactants of this kind preferably include at least one carboxyl group and/or sulfonic acid group and/or sulfate group. It has proven preferable in the context of the present invention, if the cleansing compositions include at least one specific anionic surfactant. Preferred cleansing compositions of the present invention are therefore characterized in that the cosmetic agents include at least one anionic surfactant from the group comprising (i) alkyl (ether) sulfates having 8 to 18 carbon atoms in the alkyl chain and 0 or 1 to 6 ethylene oxide units, (ii) $C_{12}$-$C_{18}$ alkyl ether carboxylates, (iii) $C_{12}$-$C_{18}$ acyl isethionates, (iv) $C_{12}$-$C_{18}$ acyl sarcosinates, (v) $C_{12}$-$C_{18}$ acyl taurines, and (vi) mixtures thereof.

Cationic surfactants according to the invention are understood to be surfactants with exclusively cationic charges. Surfactants of this kind include at least one quaternary ammonium group. According to the invention, specific cationic surfactants are used with preference. It is therefore advantageous in the context of the present invention, if they include at least one cationic surfactant from the group comprising (i) quaternized carboxylic acid triethanolamine ester salts, (ii) quaternized salts of carboxylic acids with diethanol alkylamines, (iii) quaternized salts of carboxylic acids with 1,2-dihydroxypropyl dialkylamines, (iv) quaternium-92, (v) $C_{10}$-$C_{22}$ alkyl trimethylammonium chlorides, and (vi) mixtures thereof.

Amphoteric surfactants are divided into ampholytic surfactants and zwitterionic surfactants. Ampholytic surfactants are understood to be surface-active compounds that have both acidic (for example, —COOH or —$SO_3H$ groups) and basic hydrophilic groups (for example, amino groups) and therefore, depending on the conditions, exhibit acidic or basic behavior. The skilled artisan understands zwitterionic surfactants to be surfactants that carry both a negative and positive charge in the same molecule. The use of specific amphoteric surfactants has proven advantageous according to the invention. Preferred cleansing compositions of the present invention are therefore characterized in that they include at least one amphoteric surfactant from the group comprising (i) $C_{10}$-$C_{18}$ alkyl betaines, (ii) $C_{8-12}$ alkyl amido ($C_{1-4}$) alkyl betaines, (iii) $C_{10}$-$C_{18}$ alkyl sulfobetaines, (iv) $C_{10}$-$C_{18}$ alkyl amphoacetates and amphodiacetates, (v) $C_{10}$-$C_{18}$ alkyl amphopropionates and dipropionates, and (vi) mixtures thereof.

Nonionic surfactants according to the invention are understood to be surfactants that have no charged groups. Charged groups are understood to be both permanently cationic and anionic groups and also temporarily cationic and anionic groups. Permanently cationic and anionic groups independent of the pH have a cationic or anionic charge. In contrast, temporarily cationic and anionic groups have a cationic or anionic charge only at certain pH values. It is preferred according to the invention, if the cleansing composition includes at least one nonionic surfactant from the group comprising (i) $C_{10}$-$C_{18}$ alkyl polyglucosides, (ii) sorbitan esters and sorbitan ether esters, (iii) $C_{10}$-$C_{18}$ carboxylic acid monoethanolamides, (iv) $C_{10}$-$C_{18}$ alcohol ethoxylates with 2 to 40 mol of ethylene oxide and/or propylene oxide per mole of alcohol, (v) $C_{10}$-$C_{18}$ amine oxides, (vi) glyceryl cocoates with 2 to 40 mol of ethylene oxide and/or propylene oxide per mole of glyceryl cocoate, and (vii) mixtures thereof.

Advantageously, the at least one surfactant is used in specific amount ranges in the cleansing compositions of the invention. Preferred cleansing compositions of the present invention are therefore characterized in that they include, based on their total weight, 0.5 to 60% by weight, preferably 1.0 to 50% by weight, primarily 1.5 to 40% by weight, in particular 2.0 to 30% by weight of at least one surfactant, selected from the group comprising anionic surfactants, cationic surfactants, amphoteric surfactants, nonionic surfactants, and mixtures thereof. The use of the aforementioned amounts assures a sufficient cleansing action, foam quality, foam quantity, and lather amount. Furthermore, these amounts have no negative effect on the preserving action of the preservative combination.

The cleansing compositions of the invention include as the second essential ingredient b) at least one specific preservative mixture. These preservative mixtures have a synergistic effect in regard to the antimicrobial action and therefore result in an especially effective preserving of the cleansing compositions of the invention. Furthermore, because of the synergistic effect thereof, the quantity used can be reduced, so that low-irritant and low-sensitizing cleansing compositions are obtained. Moreover, the use of the preservative mixture improves the foam quality, foam quantity, and lather amount.

The cleansing compositions of the invention preferably have a specific weight ratio of the preservatives included in this cleansing composition. It is therefore preferred in the context of the present invention, if the cleansing composition has a weight ratio of the first preservative to the second preservative in preservative mixture b) of 10:1 to 1:10, preferably of 8:1 to 1:8, primarily of 5:1 to 1:5, in particular of 2:1 to 1:2. The use of such weight ratios has proven to be especially advantageous in regard to the synergistic increase in the preservative performance of this mixture.

The cleansing agent of the invention includes the preservative mixture preferably in specific amount ranges. Preferred cleansing compositions of the invention are therefore characterized in that they include, based on their total weight, 0.001 to 10% by weight, preferably 0.005 to 7.0% by weight, primarily 0.01 to 4.0% by weight, in particular 0.05 to 2.0 by weight of at least one preservative mixture b). The aforementioned amounts refer to the total amount of the preservative mixture, i.e., the mixture of the aforementioned two preservatives. The use of such amounts of the preservative mixture leads to an excellent preserving of the cleansing compositions of the invention. Furthermore, because of the synergistic actions of the preservative mixture, the amount used thereof can be reduced without negatively influencing the preserving performance. The cleansing compositions of the invention are therefore especially low-irritant and low-sensitizing.

The cleansing compositions of the invention include as the third essential ingredient at least one additional preservative c), selected from the group comprising benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof, and mixtures of these preservatives. The addition of this at least one other preservative in conjunction with the aforementioned preservative combination results in a synergistic increase in the preserving performance.

It can be preferred in the context of the present invention, however, if a mixture of the aforementioned compounds is used as preservative c). Preferred cleansing compositions of the invention are therefore characterized in that they include at least one other preservative c), selected from the group comprising benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof.

Other preferred cleansing compositions of the invention are characterized in that they include at least two other preservatives c), selected from the group comprising benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof.

In addition, cleansing compositions according to the invention are advantageous that include at least three other preservatives c), selected from the group comprising benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof.

Lastly, the cleansing compositions of the invention are preferred that include as a further preservative c) a mixture of benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, and citric acid.

Particularly preferably, the cleansing compositions of the invention include as an additional preservative c) the preservatives listed in the table on pages 7 to 10 of the priority document, DE 102015225004.0 filed Dec. 11, 2015, which is hereby incorporated by reference, or mixtures of these preservatives KM1 to KM466.

It is advantageous in this regard if the at least one additional preservative c) is used in a specific total amount. It is therefore preferred according to the invention if the cosmetic agents include, based on their total weight, 0.001 to 10% by weight, preferably 0.005 to 9.0% by weight, primarily 0.05 to 8.0% by weight, in particular 0.1 to 7.0% by weight of at least one other preservative c). If more than one additional preservative c) is used, the total amounts given above refer to the mixture of these preservatives. The use of such amounts of the at least one additional preservative in combination with the at least one preservative mixture b) results in a synergistic increase in the preservative performance.

Particularly preferred embodiments AF1 to AF579 of cosmetic agents of the invention are given in the table on pages 11 to 25 of the priority document (all quantities are given in % by weight). Here, c stands for chloroxylenol, p for phenoxyisopropanol, u for undecylenic acid, a for formic acid, pi for piroctone olamine, s for sulfite, h for hexetidine, e for ethyl lauroyl arginate*HCl, ch for chlorphenesin, b for benzyl alcohol, AnionT for anionic surfactant, CationT for cationic surfactant, nioT for nonionic surfactant, and amphoT for amphoteric surfactant. In the table, therefore, the term (c+p) (1:2) stands for a mixture of chloroxylenol and phenoxyisopropanol in the weight ratio of 1:2 (based on the total weight of the mixture). (c+p)+(u+a) stands for the combination of a mixture of chloroxylenol and phenoxyisopropanol with a mixture of undecylenic acid and formic acid. AnionT+CationT accordingly stand for a mixture of an anionic and an amphoteric surfactant. The aforementioned preservatives or preservative mixtures KM1 to KM466 are used as an additional preservative c) (designated as KM in the table).

In embodiments AF1 to AF579, preferably the aforementioned anionic, cationic, amphoteric, and nonionic surfactants are used as surfactants. The cosmetic agents AF1 to AF579 have good cleansing action and excellent preservation. The amount of the preservatives employed can be reduced due to their synergistic action without negatively influencing the preservative action. Therefore, the cosmetic compositions of the invention are low-irritant and low-sensitizing. Furthermore, the foam quality and lather amount can be improved by the use of the aforementioned preservative mixture, so that the use thereof does not result in a negative effect on the cleansing properties.

In addition to components a) to c) mandatory according to the invention, the cleansing compositions of the invention and all other components, known to the skilled artisan for such cosmetic compositions, can be used in principle. Other active substances, auxiliary substances, and additives are, for example:

- thickeners such as gelatin or plant gum, for example, agar-agar, guar gum, alginates, xanthan gum, gum arabic, karaya gum, locust bean gum, flaxseed gums, dextrans, cellulose derivatives, e.g., methyl cellulose, hydroxyalkyl cellulose, and carboxymethyl cellulose, starch fractions and derivatives such as amylose, amylopectin, and dextrins, fully synthetic hydrocolloids such as, e.g., polyvinyl alcohol,
- structurants such as maleic acid and lactic acid,
- solvents and solubilizers such as ethanol, isopropanol, ethylene glycol, propylene glycol, glycerol, and diethylene glycol,
- fiber structure-improving active substances, particularly mono-, di-, and oligosaccharides such as, for example, glucose, galactose, fructose, fruit sugar, and lactose,
- dyes for coloring the agent,
- substances for adjusting the pH, such as, for example, α- and β-hydroxycarboxylic acids,
- active substances such as allantoin and bisabolol,
- complexing agents such as EDTA, NTA, β-alaninediacetic acid, and phosphonic acids,
- ceramides. Ceramides are understood to be N-acylsphingosine (fatty acid amides of sphingosine) or synthetic analogs of such lipids (so-called pseudo-ceramides),
- opacifiers such as latex, styrene/PVP and styrene/acrylamide copolymers,
- pearlescent agents such as ethylene glycol mono- and distearate and PEG-3 distearate,
- pigments,
- propellants such as propane-butane mixtures, $N_2O$, dimethyl ether, $CO_2$, and air,
- viscosity regulators such as salts (NaCl),
- cationic, nonionic, and amphoteric polymers,
- vitamins, in particular from groups A, B, C, E, F, and H,
- UV filters, in particular benzophenone, p-aminobenzoic acid amphoT, diphenylacrylic acid esters, cinnamic acid esters, salicylic acid esters, benzimidazoles, and o-aminobenzoic acid esters,
- protein hydrolysates and cationized protein hydrolysates,
- humectants or penetration aids and/or swelling agents, in particular urea and urea derivatives, guanidine and derivatives thereof, arginine and derivatives thereof, water glass, imidazole and derivatives thereof, histidine and derivatives thereof, benzyl alcohol, glycol ethers, propylene glycol ethers, for example, propylene glycol monoethyl ether, carbonates, hydrogen carbonates, 1,2-diols, and 1,3-diols,
- plant extracts, for example, from green tea, white tea, oak bark, stinging nettle, witch hazel, hops, chamomile, burdock, horsetail, whitethorn, lime blossom, lychee, almond, aloe vera, spruce needles, horse chestnut, sandalwood, juniper, coconut, mango, apricot, lemon, wheat, kiwi, melon, orange, grapefruit, sage, rosemary, birch, mallow, cuckoo flower, wild thyme, yarrow, thyme, melissa, restharrow, coltsfoot, marshmallow, ginseng, ginger root, *Echinacea purpurea, Olea europaea, Foeniculum vulgaris* and *Apium graveolens*,
- silicone oils, in particular polyalkylsiloxanes, polyarylsiloxanes, and polyalkylarylsiloxanes, which can be functionalized optionally with organic groups and/or ethoxy and/or propoxy groups.

The aforementioned other ingredients can be included, based on the total weight of the cleansing composition, in a total amount of 0.001 to 50% by weight, preferably of 0.01 to 40% by weight, primarily of 0.1 to 30% by weight, in particular of 0.5 to 20% by weight.

Lastly, a second subject of the present invention is the use of a cleansing composition of the invention for the cleansing and care of skin and hair.

The statements made about the cleansing compositions of the invention apply mutatis mutandis in regard to other preferred embodiments of the method of the invention, in particular in regard to the cleansing compositions used there.

The statements made about the cleansing composition of the invention apply mutatis mutandis in regard to other embodiments of the use of the invention.

The following examples explain the present invention without however limiting the same:

EXAMPLES

The cleansing compositions listed hereafter were prepared:

Shower Gel (Quantities are Given in % by Weight)

| Raw material | 1. | 1.2 | 1.3 | 1.4 | 1.5 | 1.6 |
|---|---|---|---|---|---|---|
| Sodium laureth sulfate | 9.50 | 9.50 | 9.50 | 9.50 | 9.50 | 9.50 |
| Disodium cocoamphodiacetate | 1.56 | 1.56 | 1.56 | 1.56 | 1.56 | 1.56 |
| Cocamidopropyl betaine | 1.52 | 1.52 | 1.52 | 1.52 | 1.52 | 1.52 |
| Sodium chloride | 1.38 | 1.38 | 1.38 | 1.38 | 1.38 | 1.38 |
| Perfume | 0.62 | 0.62 | 0.62 | 0.62 | 0.62 | 0.62 |
| Glycol distearate | 0.45 | 0.45 | 0.45 | 0.45 | 0.45 | 0.45 |
| Citric acid | 0.37 | 0.37 | 0.37 | 0.37 | 0.37 | 0.37 |
| PEG-7 glyceryl cocoate | 0.30 | 0.30 | 0.30 | 0.30 | 0.30 | 0.30 |
| Cocamide MEA | 0.23 | 0.23 | 0.23 | 0.23 | 0.23 | 0.23 |
| Chloroxylenol | 0.50 | — | — | — | — | 0.50 |
| Ethyl lauroyl arginate *HCl | 0.40 | — | — | — | — | 0.40 |
| Sodium sulfite | — | 0.20 | — | 0.20 | — | 0.20 |
| Hexetidine | — | 0.10 | — | — | — | 0.10 |
| Formic acid | — | — | 0.50 | — | — | 0.50 |
| Phenoxyisopropanol | — | — | 1.00 | — | 0.80 | 1.00 |
| Undecylenic acid | — | — | — | — | 0.20 | 0.20 |
| Piroctone olamine | — | — | — | 0.50 | — | 0.50 |
| Benzyl alcohol | — | — | — | — | — | 1.00 |
| Chlorphenesin | — | — | — | — | — | 0.30 |
| Benzoic acid | 0.20 | — | — | — | — | 0.20 |
| Phenoxyethanol | — | 0.50 | 0.40 | — | — | 0.50 |
| Methylparaben | — | — | — | — | 0.20 | 0.20 |
| Ethylparaben | — | — | — | — | 0.10 | 0.10 |

-continued

| Raw material | 1. | 1.2 | 1.3 | 1.4 | 1.5 | 1.6 |
|---|---|---|---|---|---|---|
| Propionic acid | — | — | — | — | — | 2.00 |
| Sorbic acid | 0.60 | — | — | — | — | 0.60 |
| Polyaminopropyl biguanide | — | — | 0.30 | — | 0.30 | 0.30 |
| Climbazole | — | 0.50 | — | — | — | 0.50 |
| Chlorhexidine | — | — | — | — | 0.30 | 0.30 |
| Glutaral | — | — | 0.10 | — | — | 0.10 |
| Salicylic acid | 0.50 | — | — | — | — | 0.50 |
| Benzalkonium chloride | — | 0.10 | — | — | — | 0.10 |
| KM [1] | — | — | — | 1.5 | — | — |
| PEG-40 hydrogenated castor oil | 0.20 | 0.20 | 0.20 | 0.20 | 0.20 | 0.20 |
| Polyquaternium-7 | 0.14 | 0.14 | 0.14 | 0.14 | 0.14 | 0.14 |
| Laureth-10 | 0.09 | 0.09 | 0.09 | 0.09 | 0.09 | 0.09 |
| Laureth-2 | 0.05 | 0.05 | 0.05 | 0.05 | 0.05 | 0.05 |
| Propylene glycol | 0.02 | 0.02 | 0.02 | 0.02 | 0.02 | 0.02 |
| PEG-55 propylene glycol oleate | 0.02 | 0.02 | 0.02 | 0.02 | 0.02 | 0.02 |
| Niacinamide | 0.01 | 0.01 | 0.01 | 0.01 | 0.01 | 0.01 |
| CI 17200 | 0.00 | 0.00 | 0.00 | 0.00 | 0.00 | 0.00 |
| CI 42090 | 0.00 | 0.00 | 0.00 | 0.00 | 0.00 | 0.00 |
| Water | To 100 | To 100 | To 100 | To 100 | To 100 | To 100 |

[1] Preservative mixture, selected at least from one of the aforementioned preservative mixtures KM1 to 466

Liquid Soap (Quantities are Given in % by Weight)

| Raw material | 2.1 | 2.2 | 2.3 | 2.4 | 2.5 | 2.6 |
|---|---|---|---|---|---|---|
| Sodium laureth sulfate | 5.60 | 5.60 | 5.60 | 5.60 | 5.60 | 5.60 |
| Cocamidopropyl betaine | 3.80 | 3.80 | 3.80 | 3.80 | 3.80 | 3.80 |
| Glycerin | 1.19 | 1.19 | 1.19 | 1.19 | 1.19 | 1.19 |
| Sodium chloride | 0.90 | 0.90 | 0.90 | 0.90 | 0.90 | 0.90 |
| Perfume | 0.67 | 0.67 | 0.67 | 0.67 | 0.67 | 0.67 |
| PEG-7 glyceryl cocoate | 0.30 | 0.30 | 0.30 | 0.30 | 0.30 | 0.30 |
| Styrene/acrylates copolymer | 0.30 | 0.30 | 0.30 | 0.30 | 0.30 | 0.30 |
| Citric Acid | 0.23 | 0.23 | 0.23 | 0.23 | 0.23 | 0.23 |
| Ethyl lauroyl arginate*HCl | 0.40 | — | — | — | 0.40 | 0.40 |
| Piroctone olamine | 1.00 | — | — | — | — | 1.00 |
| Sodium sulfite | — | — | — | — | — | 0.20 |
| Hexetidine | — | — | — | 0.10 | 0.10 | 0.10 |
| Formic acid | — | — | 0.50 | — | — | 0.50 |
| Phenoxyisopropanol | — | 1.00 | — | — | — | 1.00 |
| Undecylenic acid | — | — | 0.20 | — | — | 0.20 |
| Chloroxylenol | — | 0.50 | — | — | — | 0.50 |
| Benzyl alcohol | — | — | — | 1.00 | — | 1.00 |
| Chlorphenesin | — | — | — | — | — | 0.30 |
| Benzoic acid | — | — | — | — | — | 0.20 |
| Phenoxyethanol | 0.50 | — | — | — | — | 0.50 |
| Methylparaben | — | — | — | — | — | 0.20 |
| Ethylparaben | — | — | 0.10 | — | — | 0.10 |
| Propionic acid | — | — | — | — | — | 2.00 |
| Sorbic acid | — | 0.60 | — | — | — | 0.60 |
| Polyaminopropyl biguanide | — | — | — | — | — | 0.30 |
| Climbazole | — | — | — | — | — | 0.50 |
| Chlorhexidine | — | — | — | — | — | 0.30 |
| Glutaral | — | — | — | — | — | 0.10 |
| Salicylic acid | 0.20 | 0.20 | 0.20 | — | — | 0.50 |
| Benzalkonium chloride | — | — | — | — | — | 0.10 |
| KM [1] | — | — | — | 0.5 | 2.0 | — |
| Yogurt | 0.05 | 0.05 | 0.05 | 0.05 | 0.05 | 0.05 |
| Laureth-2 | 0.05 | 0.05 | 0.05 | 0.05 | 0.05 | 0.05 |
| Hexyl salicylate | 0.03 | 0.03 | 0.03 | 0.03 | 0.03 | 0.03 |
| Propylene glycol | 0.02 | 0.02 | 0.02 | 0.02 | 0.02 | 0.02 |
| PEG-55 propylene glycol oleate | 0.02 | 0.02 | 0.02 | 0.02 | 0.02 | 0.02 |
| Niacinamide | 0.01 | 0.01 | 0.01 | 0.01 | 0.01 | 0.01 |
| *Aloe barbadensis* leaf juice | 0.01 | 0.01 | 0.01 | 0.01 | 0.01 | 0.01 |
| Water | To 100 | To 100 | To 100 | To 100 | To 100 | To 100 |

[1] Preservative mixture, selected at least from one of the aforementioned preservative mixtures KM1 to KM466

Cleansing Gel (Quantities are Given in % by Weight)

| Raw material | 3.1 | 3.2 | 3.3 | 3.4 | 3.5 | 3.6 |
|---|---|---|---|---|---|---|
| Cocamidopropyl betaine | 5.70 | 5.70 | 5.70 | 5.70 | 5.70 | 5.70 |
| Caprylyl/capryl glucoside | 3.18 | 3.18 | 3.18 | 3.18 | 3.18 | 3.18 |
| Decyl glucoside | 2.65 | 2.65 | 2.65 | 2.65 | 2.65 | 2.65 |
| Dehydroxanthan gum | 1.19 | 1.19 | 1.19 | 1.19 | 1.19 | 1.19 |
| Sodium chloride | 1.05 | 1.05 | 1.05 | 1.05 | 1.05 | 1.05 |
| Sodium PCA | 0.50 | 0.50 | 0.50 | 0.50 | 0.50 | 0.50 |
| *Tilia platyphyllos* flower water | 0.50 | 0.50 | 0.50 | 0.50 | 0.50 | 0.50 |
| Citric acid | 0.48 | 0.48 | 0.48 | 0.48 | 0.48 | 0.48 |
| Ethyl lauroyl arginate*HCl | — | — | 0.40 | — | — | 0.40 |
| Piroctone olamine | — | 1.00 | — | — | — | 1.00 |
| Sodium sulfite | — | — | — | — | — | 0.20 |
| Hexetidine | 0.10 | — | — | — | — | 0.10 |
| Formic acid | — | — | 0.50 | 0.50 | — | 0.50 |
| Phenoxyisopropanol | — | 1.00 | — | — | 1.00 | 1.00 |
| Undecylenic acid | — | — | — | 0.20 | — | 0.20 |
| Chloroxylenol | — | — | — | — | 0.50 | 0.50 |
| Benzyl alcohol | 0.80 | — | — | — | — | 1.00 |
| Chlorphenesin | — | — | — | — | — | 0.30 |
| Benzoic acid | 0.20 | 0.20 | 0.20 | — | — | 0.20 |
| Phenoxyethanol | — | — | 0.50 | — | — | 0.50 |
| Methylparaben | — | — | — | — | — | 0.20 |
| Ethylparaben | 0.10 | — | — | — | — | 0.10 |
| Propionic acid | — | — | — | — | — | 2.00 |
| Sorbic acid | — | — | 0.60 | — | — | 0.60 |
| Polyaminopropyl biguanide | — | — | — | — | — | 0.30 |
| Climbazole | — | 0.50 | — | — | — | 0.50 |
| Chlorhexidine | 0.30 | — | — | — | — | 0.30 |
| Glutaral | — | — | — | — | — | 0.10 |
| Salicylic acid | — | — | — | — | — | 0.50 |
| Benzalkonium chloride | — | 0.10 | — | — | — | 0.10 |
| KM [1] | — | — | — | 0.2 | 1.5 | — |
| Glycerin | 0.10 | 0.10 | 0.10 | 0.10 | 0.10 | 0.10 |
| Perfume | 0.10 | 0.10 | 0.10 | 0.10 | 0.10 | 0.10 |
| Citric Acid | 0.01 | 0.01 | 0.01 | 0.01 | 0.01 | 0.01 |
| *Vitis vinifera* bud extract | 0.00 | 0.00 | 0.00 | 0.00 | 0.00 | 0.00 |
| Water | To 100 | To 100 | To 100 | To 100 | To 100 | To 100 |

[1] Preservative mixture, selected at least from one of the aforementioned preservative mixtures KM1 to KM466

Cleansing Gel (Quantities are Given in % by Weight)

| Raw material | 4.1 | 4.2 | 4.3 | 4.4 | 4.5 | 4.6 |
|---|---|---|---|---|---|---|
| Hexanediol | 5.00 | 5.00 | 5.00 | 5.00 | 5.00 | 5.00 |
| Glycerin | 4.98 | 4.98 | 4.98 | 4.98 | 4.98 | 4.98 |
| Arachidyl alcohol | 2.75 | 2.75 | 2.75 | 2.75 | 2.75 | 2.75 |
| Betaine | 2.00 | 2.00 | 2.00 | 2.00 | 2.00 | 2.00 |
| Behenyl alcohol | 1.50 | 1.50 | 1.50 | 1.50 | 1.50 | 1.50 |
| Cetearyl alcohol | 1.50 | 1.50 | 1.50 | 1.50 | 1.50 | 1.50 |
| Butylene glycol | 0.95 | 0.95 | 0.95 | 0.95 | 0.95 | 0.95 |
| Aluminum starch octenylsuccinate | 0.93 | 0.93 | 0.93 | 0.93 | 0.93 | 0.93 |
| Dimethicone | 0.90 | 0.90 | 0.90 | 0.90 | 0.90 | 0.90 |
| Propylene glycol | 0.77 | 0.77 | 0.77 | 0.77 | 0.77 | 0.77 |
| Arachidyl glucoside | 0.75 | 0.75 | 0.75 | 0.75 | 0.75 | 0.75 |
| Panthenol | 0.60 | 0.60 | 0.60 | 0.60 | 0.60 | 0.60 |
| Carbomer | 0.30 | 0.30 | 0.30 | 0.30 | 0.30 | 0.30 |
| Perfume | 0.23 | 0.23 | 0.23 | 0.23 | 0.23 | 0.23 |
| Sodium acrylate/sodium acryloyldimethyl taurate copolymer | 0.15 | 0.15 | 0.15 | 0.15 | 0.15 | 0.15 |
| Ethyl lauroyl arginate*HCl | 0.40 | — | — | 0.40 | — | 0.40 |
| Piroctone olamine | — | — | — | — | 0.50 | 1.00 |
| Sodium sulfite | — | — | — | — | — | 0.20 |
| Hexetidine | — | 0.10 | 0.10 | — | — | 0.10 |
| Formic acid | 0.40 | — | — | — | — | 0.50 |
| Phenoxyisopropanol | — | — | — | — | 1.00 | 1.00 |
| Undecylenic acid | — | — | — | 0.20 | — | 0.20 |
| Chloroxylenol | — | — | 0.50 | — | — | 0.50 |
| Benzyl alcohol | — | 1.00 | — | — | — | 1.00 |
| Chlorphenesin | — | — | — | — | — | 0.30 |
| Benzoic acid | — | — | — | — | — | 0.20 |
| Phenoxyethanol | 0.40 | 0.40 | 0.40 | — | — | 0.50 |
| Methylparaben | — | — | — | — | — | 0.20 |
| Ethylparaben | — | — | — | — | — | 0.10 |
| Propionic acid | 0.10 | — | — | — | — | 2.00 |
| Sorbic acid | — | — | — | — | — | 0.60 |
| Polyaminopropyl biguanide | — | — | 0.30 | — | — | 0.30 |
| Climbazole | — | 0.50 | — | — | — | 0.50 |
| Chlorhexidine | 0.30 | — | — | — | — | 0.30 |
| Glutaral | — | — | 0.10 | — | — | 0.10 |
| Salicylic acid | — | — | — | — | — | 0.50 |
| Benzalkonium chloride | — | 0.10 | — | — | — | 0.10 |
| KM [1] | — | — | — | 0.1 | 1.0 | — |
| Polyisobutene | 0.11 | 0.11 | 0.11 | 0.11 | 0.11 | 0.11 |
| Yogurt | 0.10 | 0.10 | 0.10 | 0.10 | 0.10 | 0.10 |
| Allantoin | 0.10 | 0.10 | 0.10 | 0.10 | 0.10 | 0.10 |
| Bisabolol | 0.09 | 0.09 | 0.09 | 0.09 | 0.09 | 0.09 |
| *Mentha aquatica* leaf extract | 0.03 | 0.03 | 0.03 | 0.03 | 0.03 | 0.03 |
| Sorbitol | 0.03 | 0.03 | 0.03 | 0.03 | 0.03 | 0.03 |
| Tocopherol | 0.03 | 0.03 | 0.03 | 0.03 | 0.03 | 0.03 |
| Hydrogenated palm glycerides citrate | 0.02 | 0.02 | 0.02 | 0.02 | 0.02 | 0.02 |
| Sebacic acid | 0.02 | 0.02 | 0.02 | 0.02 | 0.02 | 0.02 |
| 10-Hydroxydecanoic acid | 0.02 | 0.02 | 0.02 | 0.02 | 0.02 | 0.02 |
| 1,10-Decanediol | 0.02 | 0.02 | 0.02 | 0.02 | 0.02 | 0.02 |
| Sorbitan oleate | 0.01 | 0.01 | 0.01 | 0.01 | 0.01 | 0.01 |
| Caprylyl/capryl glucoside | 0.01 | 0.01 | 0.01 | 0.01 | 0.01 | 0.01 |
| Water | To 100 | To 100 | To 100 | To 100 | To 100 | To 100 |

[1] Preservative mixture, selected at least from one of the aforementioned preservative mixtures KM1 to KM466

Cleansing Cream (Quantities are Given in % by Weight)

| Raw material | 5.1 | 5.2 | 5.3 | 5.4 | 5.5 | 5.6 |
|---|---|---|---|---|---|---|
| Sodium cocoyl isethionate | 14.85 | 14.85 | 14.85 | 14.85 | 14.85 | 14.85 |
| Stearic acid | 9.75 | 9.75 | 9.75 | 9.75 | 9.75 | 9.75 |
| Talc | 4.00 | 4.00 | 4.00 | 4.00 | 4.00 | 4.00 |
| Cocamidopropyl betaine | 3.61 | 3.61 | 3.61 | 3.61 | 3.61 | 3.61 |
| Palmitic acid | 3.00 | 3.00 | 3.00 | 3.00 | 3.00 | 3.00 |
| *Zea mays* | 2.20 | 2.20 | 2.20 | 2.20 | 2.20 | 2.20 |
| Sodium isethionate | 0.90 | 0.90 | 0.90 | 0.90 | 0.90 | 0.90 |
| Sodium chloride | 0.67 | 0.67 | 0.67 | 0.67 | 0.67 | 0.67 |
| Perfume | 0.60 | 0.60 | 0.60 | 0.60 | 0.60 | 0.60 |
| Ethyl lauroyl arginate*HCl | — | — | — | — | — | 0.40 |
| Piroctone olamine | 0.50 | 0.50 | — | — | — | 1.00 |
| Sodium sulfite | — | — | — | 0.20 | — | 0.20 |
| Hexetidine | — | 0.10 | 0.10 | — | 0.10 | 0.10 |
| Formic acid | — | — | — | — | — | 0.50 |
| Phenoxyisopropanol | 1.00 | — | — | 1.00 | — | 1.00 |
| Undecylenic acid | — | — | — | — | — | 0.20 |
| Chloroxylenol | — | — | — | — | 0.50 | 0.50 |
| Benzyl alcohol | — | — | — | — | — | 1.00 |
| Chlorphenesin | — | — | 0.30 | — | — | 0.30 |
| Dehydroacetic acid | 0.20 | 0.20 | 0.20 | — | — | 0.20 |
| Benzoic acid | 0.20 | — | — | — | — | 0.20 |
| Phenoxyethanol | — | — | — | — | — | 0.50 |
| Methylparaben | — | 0.20 | — | — | — | 0.20 |
| Ethylparaben | — | — | — | — | — | 0.10 |
| Propionic acid | 2.00 | — | — | — | — | 2.00 |
| Sorbic acid | — | — | 0.60 | — | — | 0.60 |
| Polyaminopropyl biguanide | — | — | — | — | — | 0.30 |
| Climbazole | — | — | — | — | — | 0.50 |
| Chlorhexidine | 0.30 | — | — | — | — | 0.30 |
| Glutaral | — | — | — | — | — | 0.10 |
| Salicylic acid | — | — | 0.50 | — | — | 0.50 |
| Benzalkonium chloride | — | 0.10 | — | — | — | 0.10 |
| KM [1) ] | — | — | — | 0.3 | 1.2 | — |
| Propylene Glycol | 0.28 | 0.28 | 0.28 | 0.28 | 0.28 | 0.28 |
| Citric Acid | 0.20 | 0.20 | 0.20 | 0.20 | 0.20 | 0.20 |
| Mannitol | 0.11 | 0.11 | 0.11 | 0.11 | 0.11 | 0.11 |
| Tetrasodium EDTA | 0.04 | 0.04 | 0.04 | 0.04 | 0.04 | 0.04 |
| Tocopherol | 0.03 | 0.03 | 0.03 | 0.03 | 0.03 | 0.03 |
| Hydrogenated palm glycerides citrate | 0.02 | 0.02 | 0.02 | 0.02 | 0.02 | 0.02 |
| *Camellia sinensis* leaf extract | 0.01 | 0.01 | 0.01 | 0.01 | 0.01 | 0.01 |
| Water | To 100 | To 100 | To 100 | To 100 | To 100 | To 100 |

[1)] Preservative mixture, selected at least from one of the aforementioned preservative mixtures KM1 to KM466

Shower Gel (Quantities are Given in % by Weight)

| Raw material | 6.1 | 6.2 | 6.3 | 6.4 | 6.5 | 6.6 |
|---|---|---|---|---|---|---|
| Sodium laureth sulfate | 9.10 | 9.10 | 9.10 | 9.10 | 9.10 | 9.10 |
| Cocamidopropyl betaine | 1.90 | 1.90 | 1.90 | 1.90 | 1.90 | 1.90 |
| Sodium chloride | 1.35 | 1.35 | 1.35 | 1.35 | 1.35 | 1.35 |
| Glycerin | 1.00 | 1.00 | 1.00 | 1.00 | 1.00 | 1.00 |
| Perfume | 0.67 | 0.67 | 0.67 | 0.67 | 0.67 | 0.67 |
| PEG-7 glyceryl cocoate | 0.40 | 0.40 | 0.40 | 0.40 | 0.40 | 0.40 |
| Coco-glucoside | 1.00 | 1.00 | 1.00 | 1.00 | 1.00 | 1.00 |
| Styrene/acrylates copolymer | 0.30 | 0.30 | 0.30 | 0.30 | 0.30 | 0.30 |
| Citric Acid | 0.27 | 0.27 | 0.27 | 0.27 | 0.27 | 0.27 |
| Laureth-2 | 0.25 | 0.25 | 0.25 | 0.25 | 0.25 | 0.25 |
| Ethyl lauroyl arginate*HCl | — | — | 0.40 | 0.40 | — | 0.40 |
| Piroctone olamine | — | — | — | — | — | 1.00 |
| Sodium sulfite | — | — | — | — | 0.20 | 0.20 |
| Hexetidine | — | 0.10 | 0.10 | — | — | 0.10 |
| Formic acid | 0.50 | 0.50 | — | — | — | 0.50 |
| Phenoxyisopropanol | 1.00 | — | — | 1.00 | — | 1.00 |
| Undecylenic acid | — | — | — | — | — | 0.20 |
| Chloroxylenol | — | — | — | — | 0.50 | 0.50 |
| Benzyl alcohol | — | — | — | — | — | 1.00 |
| Chlorphenesin | — | — | — | — | — | 0.30 |
| Benzoic acid | — | 0.20 | — | — | — | 0.20 |
| Phenoxyethanol | — | — | — | — | — | 0.50 |
| Methylparaben | — | — | 0.20 | — | — | 0.20 |
| Ethylparaben | 0.10 | — | — | — | — | 0.10 |
| Propionic acid | — | — | — | — | — | 2.00 |

-continued

| Raw material | 6.1 | 6.2 | 6.3 | 6.4 | 6.5 | 6.6 |
|---|---|---|---|---|---|---|
| Sorbic acid | 0.20 | 0.20 | 0.20 | — | — | 0.60 |
| Polyaminopropyl biguanide | — | — | — | — | — | 0.30 |
| Climbazole | 0.50 | — | — | — | — | 0.50 |
| Chlorhexidine | — | 0.30 | — | — | — | 0.30 |
| Glutaral | — | — | — | — | — | 0.10 |
| Salicylic acid | — | — | — | — | — | 0.50 |
| Benzalkonium chloride | — | — | 0.10 | — | — | 0.10 |
| KM [1] | — | — | — | 0.9 | 0.25 | — |
| Caprylyl/capryl glucoside | 0.14 | 0.14 | 0.14 | 0.14 | 0.14 | 0.14 |
| Polyquaternium-7 | 0.14 | 0.14 | 0.14 | 0.14 | 0.14 | 0.14 |
| Propylene glycol | 0.10 | 0.10 | 0.10 | 0.10 | 0.10 | 0.10 |
| PEG-55 propylene glycol oleate | 0.10 | 0.10 | 0.10 | 0.10 | 0.10 | 0.10 |
| Water | 83.04 | 83.04 | 83.04 | 83.04 | 83.04 | 83.04 |

[1] Preservative mixture, selected at least from one of the aforementioned preservative mixtures KM1 to KM466

Cleaning Agents (Quantities are Given in % by Weight)

| Raw material | 7.1 | 7.2 | 7.3 | 7.4 | 7.5 | 7.6 |
|---|---|---|---|---|---|---|
| Disodium laureth sulfosuccinate | 10.00 | 10.00 | 10.00 | 10.00 | 10.00 | 10.00 |
| PEG-7 glyceryl cocoate | 3.50 | 3.50 | 3.50 | 3.50 | 3.50 | 3.50 |
| Capryl/capramidopropyl betaine | 1.40 | 1.40 | 1.40 | 1.40 | 1.40 | 1.40 |
| Propylene glycol | 1.08 | 1.08 | 1.08 | 1.08 | 1.08 | 1.08 |
| Decyl glucoside | 1.06 | 1.06 | 1.06 | 1.06 | 1.06 | 1.06 |
| Glycerin | 0.86 | 0.86 | 0.86 | 0.86 | 0.86 | 0.86 |
| Coco-glucoside | 0.85 | 0.85 | 0.85 | 0.85 | 0.85 | 0.85 |
| Glyceryl oleate | 0.73 | 0.73 | 0.73 | 0.73 | 0.73 | 0.73 |
| Sorbitol | 0.70 | 0.70 | 0.70 | 0.70 | 0.70 | 0.70 |
| Sodium PCA | 0.50 | 0.50 | 0.50 | 0.50 | 0.50 | 0.50 |
| Perfume | 0.41 | 0.41 | 0.41 | 0.41 | 0.41 | 0.41 |
| Ethyl lauroyl arginate*HCl | — | — | — | 0.40 | — | 0.40 |
| Piroctone olamine | 0.5 | — | — | — | — | 1.00 |
| Sodium sulfite | — | — | 0.20 | — | — | 0.20 |
| Hexetidine | — | — | — | — | 0.10 | 0.10 |
| Formic acid | — | — | — | 0.50 | — | 0.50 |
| Phenoxyisopropanol | 1.00 | — | — | — | — | 1.00 |
| Undecylenic acid | — | — | — | — | 0.20 | 0.20 |
| Chloroxylenol | — | 0.50 | — | — | — | 0.50 |
| Benzyl alcohol | — | 1.00 | — | — | — | 1.00 |
| Chlorphenesin | — | — | 0.30 | — | — | 0.30 |
| Benzoic acid | — | — | — | — | — | 0.20 |
| Phenoxyethanol | 0.50 | — | — | — | — | 0.50 |
| Methylparaben | — | — | — | — | — | 0.20 |
| Ethylparaben | 0.10 | — | — | — | — | 0.10 |
| Propionic acid | — | — | — | — | — | 2.00 |
| Sorbic acid | — | 0.60 | — | — | — | 0.60 |
| Polyaminopropyl biguanide | 0.30 | — | — | — | — | 0.30 |
| Climbazole | — | — | — | — | — | 0.50 |
| Chlorhexidine | — | 0.30 | — | — | — | 0.30 |
| Glutaral | — | — | — | — | — | 0.10 |
| Salicylic acid | 0.20 | 0.20 | 0.20 | — | — | 0.50 |
| Benzalkonium chloride | — | 0.10 | — | — | — | 0.10 |
| KM [1] | — | — | — | 0.7 | 0.01 | — |
| Lactic acid | 0.36 | 0.36 | 0.36 | 0.36 | 0.36 | 0.36 |
| Sodium chloride | 0.30 | 0.30 | 0.30 | 0.30 | 0.30 | 0.30 |
| Sodium lactate | 0.12 | 0.12 | 0.12 | 0.12 | 0.12 | 0.12 |
| Tetrasodium EDTA | 0.10 | 0.10 | 0.10 | 0.10 | 0.10 | 0.10 |
| Citric acid | 0.08 | 0.08 | 0.08 | 0.08 | 0.08 | 0.08 |
| *Persea gratissima* oil | 0.03 | 0.03 | 0.03 | 0.03 | 0.03 | 0.03 |
| Tocopherol | 0.03 | 0.03 | 0.03 | 0.03 | 0.03 | 0.03 |
| Hydrogenated palm glycerides citrate | 0.02 | 0.02 | 0.02 | 0.02 | 0.02 | 0.02 |
| *Persea gratissima* oil unsaponifables | 0.02 | 0.02 | 0.02 | 0.02 | 0.02 | 0.02 |
| *Prunus amygdalus dulcis* oil | 0.02 | 0.02 | 0.02 | 0.02 | 0.02 | 0.02 |
| Water | 76.97 | 76.97 | 76.97 | 76.97 | 76.97 | 76.97 |

[1] Preservative mixture, selected at least from one of the aforementioned preservative mixtures KM1 to KM466

Facial Toner (Quantities are Given in % by Weight)

| Raw material | 8.1 | 8.2 | 8.3 | 8.4 | 8.5 | 8.6 |
|---|---|---|---|---|---|---|
| Mentha piperita water | 2.99 | 2.99 | 2.99 | 2.99 | 2.99 | 2.99 |
| Glycerin | 2.10 | 2.10 | 2.10 | 2.10 | 2.10 | 2.10 |
| Cocamidopropyl betaine | 0.57 | 0.57 | 0.57 | 0.57 | 0.57 | 0.57 |
| Ethyl lauroyl arginate*HCl | — | — | 0.40 | — | 0.4 | 0.40 |
| Piroctone olamine | 1.0 | — | — | — | — | 1.00 |
| Sodium sulfite | — | — | — | — | 0.20 | 0.20 |
| Hexetidine | 0.1 | 0.10 | — | — | — | 0.10 |
| Formic acid | — | — | — | 0.50 | — | 0.50 |
| Phenoxyisopropanol | — | — | — | — | — | 1.00 |
| Undecylenic acid | — | 0.20 | 0.20 | — | — | 0.20 |
| Chloroxylenol | — | — | — | — | — | 0.50 |
| Benzyl alcohol | — | — | — | 1.00 | — | 1.00 |
| Chlorphenesin | — | — | — | — | 0.30 | 0.30 |
| Benzoic acid | — | 0.20 | — | — | — | 0.20 |
| Phenoxyethanol | 0.50 | — | 0.50 | — | — | 0.50 |
| Methylparaben | — | — | — | — | — | 0.20 |
| Ethylparaben | 0.10 | — | — | — | — | 0.10 |
| Propionic acid | — | — | 2.00 | — | — | 2.00 |
| Sorbic acid | — | 0.60 | — | — | — | 0.60 |
| Polyaminopropyl biguanide | — | — | — | — | — | 0.30 |
| Climbazole | — | — | — | — | — | 0.50 |
| Chlorhexidine | 0.20 | 0.20 | 0.20 | — | — | 0.30 |
| Glutaral | — | — | — | — | — | 0.10 |
| Salicylic acid | — | — | — | — | — | 0.50 |
| Benzalkonium chloride | 0.10 | — | — | — | — | 0.10 |
| KM [1] | — | — | — | 1.8 | 0.09 | — |
| Tilia platyphyllos flower water | 0.45 | 0.45 | 0.45 | 0.45 | 0.45 | 0.45 |
| Sodium chloride | 0.11 | 0.11 | 0.11 | 0.11 | 0.11 | 0.11 |
| Citric acid | 0.10 | 0.10 | 0.10 | 0.10 | 0.10 | 0.10 |
| Water | To 100 | To 100 | To 100 | To 100 | To 100 | To 100 |

[1] Preservative mixture, selected at least from one of the aforementioned preservative mixtures KM1 to KM466

Shower Cream (Quantities are Given in % by Weight)

| Raw material | 9.1 | 9.2 | 9.3 | 9.4 | 9.5 | 9.6 |
|---|---|---|---|---|---|---|
| Sodium laureth sulfate | 9.50 | 9.50 | 9.50 | 9.50 | 9.50 | 9.50 |
| Disodium cocoamphodiacetate | 1.56 | 1.56 | 1.56 | 1.56 | 1.56 | 1.56 |
| Cocamidopropyl betaine | 1.52 | 1.52 | 1.52 | 1.52 | 1.52 | 1.52 |
| Sodium chloride | 1.38 | 1.38 | 1.38 | 1.38 | 1.38 | 1.38 |
| Perfume | 0.62 | 0.62 | 0.62 | 0.62 | 0.62 | 0.62 |
| Glycol distearate | 0.45 | 0.45 | 0.45 | 0.45 | 0.45 | 0.45 |
| Citric acid | 0.37 | 0.37 | 0.37 | 0.37 | 0.37 | 0.37 |
| PEG-7 glyceryl cocoate | 0.30 | 0.30 | 0.30 | 0.30 | 0.30 | 0.30 |
| Cocamide MEA | 0.23 | 0.23 | 0.23 | 0.23 | 0.23 | 0.23 |
| Ethyl lauroyl arginate*HCl | — | 0.40 | — | — | — | 0.40 |
| Piroctone olamine | — | — | — | — | 1.00 | 1.00 |
| Sodium sulfite | — | — | 0.20 | — | — | 0.20 |
| Hexetidine | — | — | — | — | — | 0.10 |
| Formic acid | — | — | 0.50 | — | — | 0.50 |
| Phenoxyisopropanol | 1.0 | — | — | 1.00 | — | 1.00 |
| Undecylenic acid | — | — | 0.20 | — | — | 0.20 |
| Chloroxylenol | 0.50 | — | — | — | — | 0.50 |
| Benzyl alcohol | — | — | — | 1.00 | — | 1.00 |
| Chlorphenesin | — | 0.30 | — | — | 0.30 | 0.30 |
| Benzoic acid | 0.20 | 0.20 | 0.20 | — | — | 0.20 |
| Phenoxyethanol | 0.50 | — | — | — | — | 0.50 |
| Methylparaben | — | — | — | — | — | 0.20 |
| Ethylparaben | — | 0.10 | — | — | — | 0.10 |
| Propionic acid | — | — | — | — | — | 2.00 |
| Sorbic acid | — | — | — | — | — | 0.60 |
| Polyaminopropyl biguanide | 0.30 | — | — | — | — | 0.30 |
| Climbazole | — | — | 0.50 | — | — | 0.50 |
| Chlorhexidine | — | — | — | — | — | 0.30 |
| Glutaral | — | 0.10 | — | — | — | 0.10 |
| Salicylic acid | — | — | — | — | — | 0.50 |
| Benzalkonium chloride | — | — | 0.10 | — | — | 0.10 |
| KM [1] | — | — | — | 0.001 | 0.4 | — |
| PEG-40 hydrogenated castor oil | 0.20 | 0.20 | 0.20 | 0.20 | 0.20 | 0.20 |
| Polyquaternium-7 | 0.14 | 0.14 | 0.14 | 0.14 | 0.14 | 0.14 |
| Laureth-10 | 0.09 | 0.09 | 0.09 | 0.09 | 0.09 | 0.09 |
| Laureth-2 | 0.05 | 0.05 | 0.05 | 0.05 | 0.05 | 0.05 |
| Propylene glycol | 0.02 | 0.02 | 0.02 | 0.02 | 0.02 | 0.02 |
| PEG-55 propylene glycol oleate | 0.02 | 0.02 | 0.02 | 0.02 | 0.02 | 0.02 |
| Water | To 100 | To 100 | To 100 | To 100 | To 100 | To 100 |

[1] Preservative mixture, selected at least from one of the aforementioned preservative mixtures KM1 to KM466

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cleansing composition, containing in a cosmetically acceptable carrier
   a) at least one surfactant, selected from the group consisting of anionic surfactants, cationic surfactants, amphoteric surfactants, nonionic surfactants, and mixtures thereof,
   b) at least one preservative mixture, selected from the group consisting of
      phenoxyisopropanol and formic acid,
      sulfite(s) and hexetidine,
      ethyl lauroyl arginate and formic acid,
      ethyl lauroyl arginate and chloroxylenol,
      hexetidine and benzyl alcohol,
      hexetidine and chloroxylenol,
      hexetidine and formic acid,
      and mixtures thereof, and
   c) at least two other preservatives, selected from the group consisting of benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof, and mixtures of such preservatives.

2. The cleansing composition according to claim 1, wherein the at least one surfactant is included at a concentration of 0.5 to 60% by weight, based on the total weight of the cleansing composition.

3. The cleansing composition according to claim 1, wherein the at least one surfactant includes an anionic surfactant selected from the group consisting of (i) alkyl (ether) sulfates having 8 to 18 carbon atoms in the alkyl chain and 1 to 6 ethylene oxide units, (ii) $C_{12}$-$C_{18}$ alkyl ether carboxylates, (iii) $C_{12}$-$C_{18}$ acyl isethionates, (iv) $C_{12}$-$C_{18}$ acyl sarcosinates, (v) $C_{12}$-$C_{18}$ acyl taurines, and (vi) mixtures thereof.

4. The cleansing composition according to claim 1, wherein the at least one surfactant includes at least one cationic surfactant selected from the group consisting of (i) quaternized carboxylic acid triethanolamine ester salts, (ii) quaternized salts of carboxylic acids with diethanol alkylamines, (iii) quaternized salts of carboxylic acids with 1,2-dihydroxypropyl dialkylamines, (iv) quaternium-92, (v) $C_{10}$-$C_{22}$ alkyl trimethylammonium chlorides, and (vi) mixtures thereof.

5. The cleansing composition according to claim 1, wherein the at least one surfactant includes at least one amphoteric surfactant selected from the group consisting of (i) $C_{10}$-$C_{18}$ alkyl betaines, (ii) $C_{8-12}$ alkyl amido ($C_{1-4}$) alkyl betaines, (iii) $C_{10}$-$C_{18}$ alkyl sulfobetaines, (iv) $C_{10}$-$C_{18}$ alkyl amphoacetates and amphodiacetates, (v) $C_{10}$-$C_{18}$ alkyl amphopropionates and dipropionates, and (vi) mixtures thereof.

6. The cleansing composition according to claim 1, wherein the at least one surfactant includes at least one nonionic surfactant selected from the group consisting of (i) $C_{10}$-$C_{18}$ alkyl polyglucosides, (ii) sorbitan esters and sorbitan ether esters, (iii) $C_{10}$-$C_{18}$ carboxylic acid monoethanolamides, (iv) $C_{10}$-$C_{18}$ alcohol ethoxylates with 2 to 40 mol of ethylene oxide and/or propylene oxide per mole of alcohol, (v) $C_{10}$-$C_{18}$ amine oxides, (vi) glyceryl cocoates with 2 to 40 mol of ethylene oxide and/or propylene oxide per mole of glyceryl cocoate, and (vii) mixtures thereof.

7. The cleansing composition according to claim 1, wherein a weight ratio of the first preservative to the second preservative in the preservative mixture b) is between 10:1 to 1:10.

8. The cleansing composition according to claim 1, wherein the at least one preservative mixture b) is included at a concentration of 0.001 to 10% by weight, based on the total weight of the cleansing composition.

9. The cleansing composition according to claim 1, wherein the at least two other preservatives c) is at least three such other preservatives.

10. The cleansing composition according to claim 1, wherein the at least two other preservatives c) is at least four such other preservatives.

11. The cleansing composition according to claim 1, wherein the at least two other preservatives c) is included at a concentration of 0.001 to 10% by weight based on the total weight of the cleansing composition.

12. A method for preserving a surfactant-containing cleansing composition, including providing the cleansing composition with a preservative combination consisting of
   at least one preservative mixture, selected from the group consisting of phenoxyisopropanol and formic acid, sulfite(s) and hexetidine, ethyl lauroyl arginate and formic acid, ethyl lauroyl arginate and chloroxylenol, hexetidine and benzyl alcohol, hexetidine and chloroxylenol, hexetidine and formic acid, and mixtures thereof, and
   at least two other preservatives, selected from the group consisting of benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof, and mixtures of such preservatives.

13. A cleansing composition, in a cosmetically acceptable carrier, comprising
   at least one surfactant, selected from the group consisting of anionic surfactants, cationic surfactants, amphoteric surfactants, nonionic surfactants, and mixtures thereof, and
   a combination of preservatives consisting of:
      a first preservative mixture selected from the group consisting of
         phenoxyisopropanol and piroctone olamine,
         phenoxyisopropanol and formic acid,
         sulfite(s) and hexetidine,
         ethyl lauroyl arginate and formic acid,
         ethyl lauroyl arginate and chloroxylenol,
         hexetidine and benzyl alcohol,
         hexetidine and chloroxylenol,
         hexetidine and piroctone olamine,
         hexetidine and chlorophenesin, hexetidine and formic acid,
and mixtures thereof; and
at least two additional preservatives selected from the group consisting of benzoic acid and salts thereof, propionic acid and salts thereof, salicylic acid and salts thereof, sorbic acid and salts thereof, zinc salts, paraben(s), polyaminopropyl biguanide, phenoxyethanol, climbazole, chlorhexidine and salts thereof, quaternary ammonium compounds, glutaral, citric acid and salts thereof, and mixtures of such preservatives.

* * * * *